United States Patent [19]

Hoffmann et al.

[11] Patent Number: 4,880,740

[45] Date of Patent: Nov. 14, 1989

[54] MICROBIAL REDUCTION OF IRON ORE

[75] Inventors: Michael R. Hoffmann; Robert G. Arnold; Gregory Stephanopoulos, all of Pasadena, Calif.

[73] Assignee: California Institute of Technology, Pasadena, Calif.

[21] Appl. No.: 661,629

[22] Filed: Oct. 17, 1984

Related U.S. Application Data

[63] Continuation-in-part of Ser. No. 626,911, Jul. 2, 1984, abandoned.

[51] Int. Cl.$^4$ .................................................. C12P 3/00
[52] U.S. Cl. ...................................... 435/168; 435/262
[58] Field of Search ................................. 435/168, 262

[56] References Cited

PUBLICATIONS

Chemical Abstracts, vol. 86 (1977); #2180h, Brock et al.
Chemical Abstracts, vol. 81 (1974); #47223n, Galstyan et al.
Chemical Abstracts, vol. 95 (1981); #165319k, Shakhobova.
Chemical Abstracts, vol. 98 (1983); #113276m, Jones et al.
Brierley, C. L. (1982), Microbiological Mining, *Scientific Am.*, 247, 44–53.
Brock, T. D. and J. Gustafson (1976), Ferric Iron Reduction by Sulfur and Iron-Oxidizing Bacteria, *Appl. Environ. Microbiol.*, 32, 567–571.
Ehrlich, H. L. (1981), *Geomicrobiology*, Marcel Dekker, New York, p. 187.
Kino, K. and S. Usami (1982), Biological Reduction of Ferric Iron and Sulfur Oxidizing Bacteria, *Agric. Biol. Chem.*, 46, 803–805.
Metcalf & Eddy, Inc. (1979), *Wastewater Engineering: Treatment, Disposal, Reuse,* 2nd edition, McGraw-Hill, New York, 56–75.
Murr, L. E., A. E. Torma and J. A. Brierley (1978), *Metallurgical Applications of Bacterial Leaching and Related Phenomena,* Academic Press, New York, 526 pages, pp. 403–426.
Obuekwe, C. E. and W. S. Westlake (1982), Effects of Medium Composition on Cell Pigmentation, Cytochrome Content, and Ferric Iron Reduction in a Pseudomonas sp. Isolated From Crude Oil, *Can. J. Microbiol.*, 28, 989–992.
Jones, Gardener and Simon (1983), Bacterial Reduction of Ferric Iron in a Stratified Eutophic Lake, *J. General Microbiol.*, 129, 131–139.
Munch and Ottow (1983), Reductive Transformation Mechanism of Ferric Oxides in Hydromorphic Soils, *Environ. Biogeochemistry Ecol. Bull.* (Stockholm), 35, 383–394.
Hoffmann, Faust, Panda, Koo and Tsuchiya (1981), Kinetics of the Removal of Iron Pyrite From Coal by Microbial Catalysis, *Appl. Environ. Microbiol.*, 42, 259–271.

*Primary Examiner*—Leonard Schenkman
*Assistant Examiner*—Joseph A. Lipovsky
*Attorney, Agent, or Firm*—F. Eugene Logan

[57] ABSTRACT

A process is provided for reducing iron ore by treatment with microorganisms which comprises forming an aqueous mixture of iron ore, microorganisms operable for reducing the ferric iron of the iron ore to ferrous iron, and a substrate operable as an energy source for the microbial reduction; and maintaining the aqueous mixture for a period of time and under conditions operable to effect the reduction of the ore. Preferably the microorganism is Pseudomonas sp. 200 and the reduction conducted anaerobically with a domestic wastewater as the substrate. An aqueous solution containing soluble ferrous iron can be separated from the reacted mixture, treated with a base to precipitate ferrous hydroxide which can then be recovered as a concentrated slurry.

33 Claims, 11 Drawing Sheets

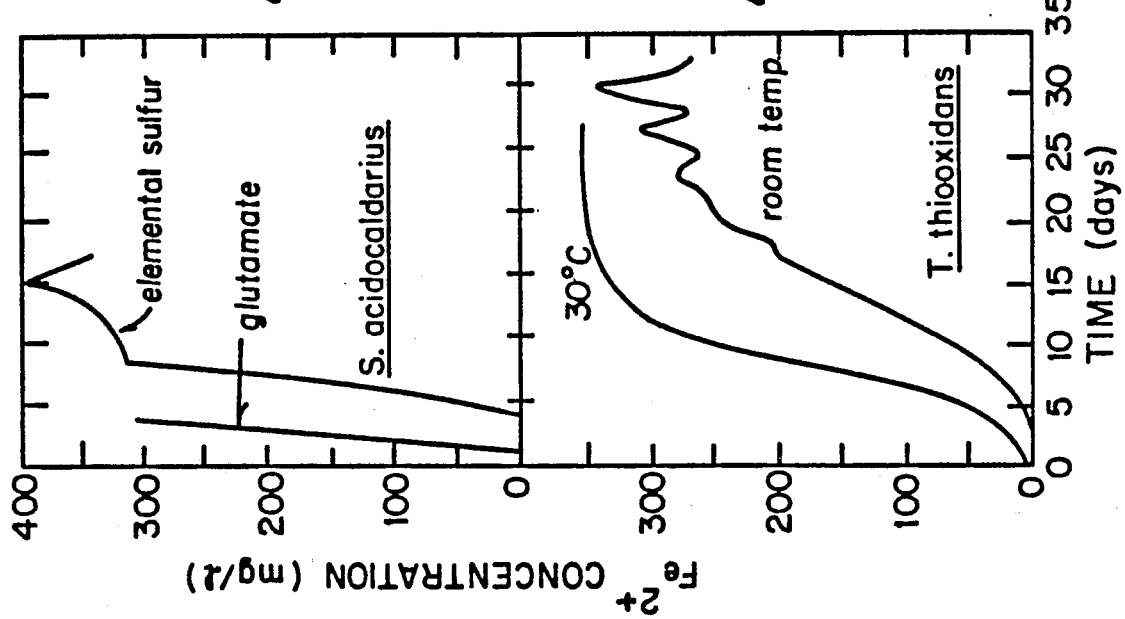
FIG. 1B
FIG. 1C
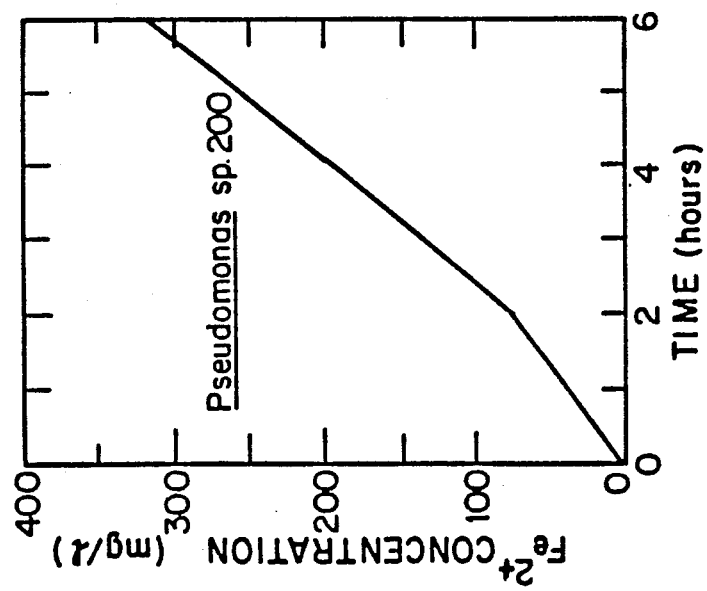
FIG. 1A

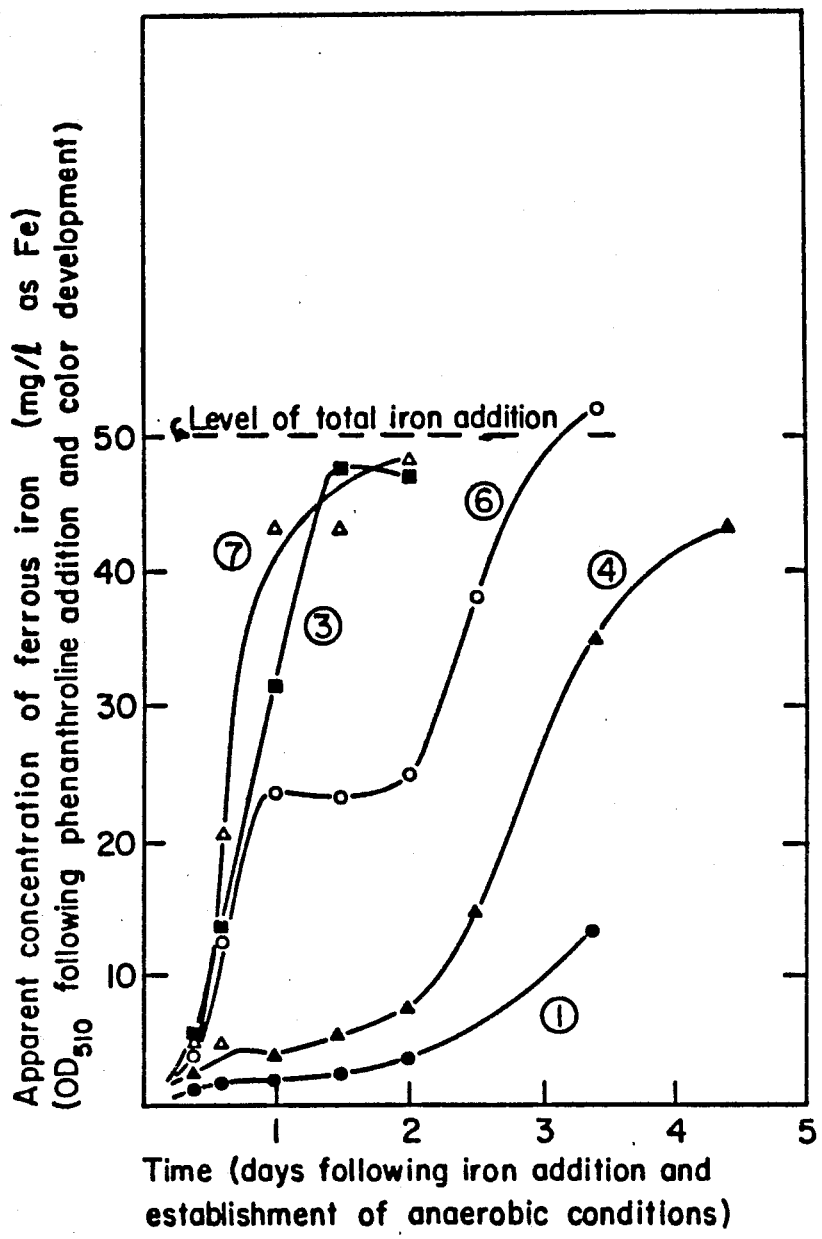

Iron Reduction by *Pseudomonas aeruginosa* in the Presence of Varied Concentrations of Citrate Ligand.

1) Control -- no citrate added.

3) Citrate concentration = 5x initial iron concentration on molar basis (ligand added as sodium citrate).

4) Citrate concentration = 0.2x initial iron concentration on molar basis (ligand added as citric acid).

6) Citrate concentration = 1.0x initial iron concentration on molar basis (ligand added as citric acid).

7) Citrate concentration = 5x initial iron concentration on molar basis (ligand added as sodium citrate).

FIG. 10 the intervening years, a similar cost today could easily be twice as high.

In 1976, the unit cost of coking coal in the U.S. was $53.73 per ton of steel produced. During steel production, coke is introduced to maintain reducing conditions necessary for production of elemental iron from iron oxides. Prereduction of iron(III) oxides to iron(II) would result in significant savings in coke demand. Our preliminary economic analysis has lead us to believe that microbial extraction and beneficiation of iron ore can be economically attractive. It is an object of this invention to utilize microorganisms for the reductive dissolution of iron from iron ore. It is a further object to carry out such reduction at a cost comparable to conventional coke/steel processes.

4,880,740

MICROBIAL REDUCTION OF IRON ORE

The work resulting in this invention was supported by the U.S. Department of Energy under Project Agreement DE-AT03-83ER13125 under Contract Number DE-AM03-76SF00767.

This is a continuation-in-part application of Ser. No. 626,911 filed July 2, 1984, now abandoned.

BACKGROUND

Microorganisms are exploited by man for the production of a wide range of products. Alcohols, antibiotics, vitamins, food supplements and many specialty chemicals are a few of the products derived principally from microbial production. In addition, microorganisms are crucial to domestic and industrial wastewater treatment and important within ecological and geochemical cycles. Bacteria have been used by the minerals industry to leach metals from ores by oxidative dissolution (Murr et al., 1976). In the copper mining industry, dump leaching has been carried out on a large scale using the rod-shaped bacterium *Thiobacillus ferrooxidans* (Brierley, 1982). The exploitation of microorganisms to perform specific and otherwise difficult industrial tasks will most likely increase as progress in genetic manipulation continues.

Among the many remarkable and potentially very useful microbial transformations are those that are geologically important. The study of microbial biogeochemistry has defined many bioredox, bioprecipitation, and biosolution reactions and has resulted in classification of microorganisms responsible for these processes.

A number of microorganisms catalyze the dissimilative reduction of iron ores (Ehrlich, 1981). Commercial application of microbial extraction, from a systematic exploitation of these organisms and biologically catalyzed reactions would be of great benefit to the metal-producing industry. Commercial extraction of iron ore by reduction of ferric to ferrous iron through microbial action would be a boon to the steel industry.

The number of bacteria whose iron-reducing capabilities are established is fairly large. However, there are significant differences among species and classes of species in such bacteria, in terms of both efficiency and kinetics of iron reduction and the environmental conditions under which the transformation is observed.

The cost of employing microbial methods for solubilizing iron(II) from ore must be comparable to that of existing industrial methods of iron extraction and reduction if the process is to be commercially viable. In 1978, the cost of producing carbon steel in the U.S. and Japan was approximately $400 per ton. It is interesting to note that the most rapidly escalating component cost was that of materials. While still higher than in other countries, the cost of labor for steel production in the U.S. rose more slowly between 1969 and 1978 than in other major western steel producing nations. The reported average U.S. cost for iron ore was about $44.51 per ton of steel produced. It is assumed that this figure represents the total cost of extracting and pelletizing iron oxides in a form suitable for production of pig iron. Considering the general inflation rate observed during Dissimilative iron reduction has been explored by others. FIG. 1 is a graphic summary of what we believe are the most relevant published kinetic data. Iron reduction rates observed by Obuekwe and Westlake in cultures of Pseudomonas sp. 200, FIG. 1A are by far the most rapid, while those measured by Brock and Gustafson in cultures of *Sulfolubus acidocaldarius*, FIG. 1B and by Kino and Usami in cultures of *Thiobacillus thiooxidans*, FIG. 1C, are appreciably slower. The data of FIG. 1A represent iron solubilization by Pseudomonas sp. 200 grown anaerobically on complex medium at 30° C.

The data of FIG. 1B represent aerobic reduction of ferric iron by *S. acidocaldarius* at 70° C. using elemental sulfur in one experimental set, and glutamate in another set as the energy source. The data of FIG. 1C represent aerobic reduction of ferric iron by *T. thiooxidans* using elemental sulfur as the energy source at room temperature in one experimental set and at 30° C. in another set. Under experimental conditions employed, the maximum observed rates of iron reduction were 50 and 90 mg per liter-day, respectively.

The following references, some of which are referred to herein, may be of further interest to the reader.

Atkinson, Bernard and Ferda Mavituma (1983) *Biochemical Engineering and Biotechnology Handbook*, Macmillan Publishers, Ltd.

Brierley, C. L. (1982) Microbiological mining, *Scientific Am.* 247, 44–53.

Brock, T. D. and J. Gustafson (1976) Ferric iron reduction by sulfur and iron-oxidizing bacteria, *Appl. Environ. Microbiol.* 32, 567–571.

Ehrlich, H. L. (1981) *Geomicrobiology*, Marcel Dekker, New York, p. 187.

Kino, K. and S. Usami (1982) Biological reduction of ferric iron and sulfur oxidizing bacteria, *Agric. Biol. Chem.* 46, 803–805.

Metcalf & Eddy, Inc. (1979) *Wastewater Engineering: Treatment, Disposal, Reuse*, 2nd edition, McGraw-Hill, New York.

Murr, L. E., A. E. Torma and J. A. Brierley (1978) *Metallurgical Applications of Bacterial Leaching and Related Phenomena*, Academic Press, New York, 526 pages.

Obuekwe, C. O. and W. S. Westlake (1982) Effects of medium composition on cell pigmentation, cytochrome content, and ferric iron reduction in a Pseudomonas sp. isolated from crude oil, *Can. J. Microbiol.* 28, 989–992.

Stryer, Lubert (1981) *Biochemistry*, 2nd edition, W. H. Freeman and Company, San Francisco.

SUMMARY

A number of microorganisms have been studied to assess their ability to promote dissimilative iron reduction under laboratory conditions. The desired criteria for microorganism selection are (i.) iron-reduction capacities, (ii.) microorganism availability, and (iii.) convenience in establishing conditions for rapid growth. Table 1 contains a summary of these bacterial species. A number of important species traits are identified in the Table. We believe that two or more mechanisms leading to the reduction of ferric iron are active among the bacteria set forth in Table 1.

Accordingly, there is provided a process for reducing ferric iron contained in iron ore with microorganisms comprising forming an aqueous mixture which comprises (i) iron ore which contains ferric iron, (ii) microorganisms operable for reducing the ferric iron constituents in the iron ore to ferrous iron, and (iii) a substrate operable as an energy souce for the reduction of the iron ore by the microorganisms; and maintaining the aqueous mixture under conditions operable for reducing the ferric iron of the iron ore to ferrous iron by the microbial activity of the microorganisms thereby reducing the ferric iron contained in the iron ore. In one embodiment, the substrate is selected from the group consisting of carbonaceous waste products, elemental sulfur, substances containing partially reduced sulfur forms, and mixtures thereof. In one embodiment, the substrate is a carbonaceous waste product selected from the group consisting of agricultural wastes, forest industry wastes, dairy wastes, brewery wastes, chemical industry wastes, waste waters, and mixtures thereof. In one embodiment, the waste product is selected from the group consisting of sugar beet waste, sugar cane waste, rice hulls, dairy whey, tree bark, paper waste, pulp waste, domestic and industrial waste waters, and mixtures thereof. Other sources of substrate are high BOD industrial wastes such as that from textile mills, waste from poultry, meat packing or processing, fruit and vegetable processing, brewery, livestock feed lot, cannery, slaughterhouse, and other waste from pulp and papermill, dairy and beet or cane sugar manufacturing.

Typical composition of untreated domestic wastewater, as reported by Metcalf & Eddy (1978) is given below.

| Constituent | Strong | Medium | Weak |
| --- | --- | --- | --- |
| Biochemical oxygen demand, 5-day, 20° C. | 400 | 220 | 110 |
| Total organic carbon | 290 | 160 | 80 |
| Chemical oxygen demand | 1000 | 500 | 250 |
| Total nitrogen (as N) | 85 | 40 | 20 |
| Total phosphorus (as P) | 15 | 8 | 4 |

A further embodiment comprises producing the microorganisms in an aerobic environment by inoculating an aqueous growth medium with an inoculating amount of the microorganisms thereby forming a growth mixture; maintaining the growth mixture under aerobic conditions operable to substantially increase the population of the microorganisms; and introducing the thusly produced microorganisms in a feedstream into the aqueous mixture as the effective amount of the microorganisms used to form the aqueous mixture. A further embodiment comprises, comminuting iron ore to form a predetermined size range of iron ore particles.

In a still further embodiment, the ferric iron constituent which has been reduced to ferrous iron is soluble in the aqueous phase of the aqueous mixture, and the aqueous phase containing the soluble ferrous iron is separated from the mixture, and an iron-containing precipitate is formed and separated from the thusly separated aqueous phase. In a further embodiment the aqueous phase which comprises the soluble ferrous iron is treated with a reagent operable for forming a precipitate which contains a major part of the iron component of the ferrous iron, thereby forming a mixture comprising an iron-containing precipitate and an aqueous phase having a reduced amount of dissolved iron. In one embodiment, the precipitate is formed by adding a base to the separated aqueous phase to precipitate a ferrous iron precipitate. In one embodiment, the reagent used for treating the separated aqueous phase is sodium hydroxide and the iron-containing precipitate is ferrous hydroxide. In a further embodiment the process further comprises recovering a slurry which comprises the iron-containing precipitate from the mixture formed by treating the separated aqueous phase which comprises the soluble ferrous iron with the reagent operable for forming a precipitate which contains a major part of the iron component of the ferrous iron.

In one embodiment, the microbial reactor is a well-mixed continuous-flow reactor. In another embodiment, the reaction is conducted in a slurry pipeline so that the slurry pipeline used to transport the aqueous mixture becomes the microbial reactor. In another embodiment, the separating of the aqueous mixture containing the soluble ferrous iron comprises gravity separation. In another embodiment, the iron-containing precipitate is recovered, preferably, by a process comprising gravity separation. In a further embodiment, the aqueous mixture containing the soluble ferrous iron is separated into an aqueous phase which is substantially free of undissolved solids and a slurry fraction which contains substantially all the undissolved solids in the aqueous mixture. In a further embodiment, the slurry fraction is recycled to the aqueous mixture or biological reactor. A further embodiment comprises separating biomass from the aqueous mixture and recycling it to the microbial reactor.

In one embodiment, the microorganisms are selected from the group consisting of *Thiobacillus thiooxidans, Bacillus circulans, Sulfolobus acidocaldarius, Bacillus pumilus, Bacillus polymyxa, Pseudomonas aeruginosa,* Pseudomonas sp. 200, Bacillus acidocaldarius, Aerobacter aerogenes, Esherichia coli, Bacillus cereus, Bacillus mesentericus, Clostridium polymyxa, Bacillus centrosporus, Bacillus megaterium, Clostridium butyricum, Clostridium saccharobutyricum, Bacillus 29, Bacillus 29A, and mixed cultures of the aforementioned organisms. In a further embodiment, the microorganisms are strains of organisms which have been mutated or selected so that the strains have enhanced iron-reducing properties. In one embodiment, the organisms which are mutated or selected are selected from the group consisting of the above-mentioned microorganisms.

In a further embodiment, a supplementary nutrient is added to the aqueous mixture. In one embodiment, the supplementary nutrient is selected from the group consisting of phosphorous, calcium, ammonium, nitrate, molybdenum, selenium, sulfate, vitamins, and mixtures thereof.

Another embodiment for reducing ferric iron contained in iron ore by treatment with microorganisms comprises, forming an aqueous mixture with comprises (i) particles of iron ore which contain ferric iron, (ii) an effective amount of microorganisms operable for reducing the ferric iron constituent of the iron particles to ferrous iron, (iii) a substrate operable for being oxidized by the microorganisms, the substrate being supplied in an effective amount operable for providing at least a major part of the energy required by the mixture to reduce at least a major part of the ferric iron constituents of the iron ore to ferrous iron; and maintaining the aqueous mixture for a predetermined period of time under conditions of temperature and pressure, and in an anaerobic environment, operable for reducing at least a major part of the ferric iron component to ferrous iron by the microbial activity of the microorganisms thereby reducing the ferric iron contained in the iron ore. In one embodiment, the predetermined period of time is no greater than about one day and the conditions in the reactor are a temperature from about 40° F. to about 160° F., and an absolute pressure of about 1 atmosphere.

Another embodiment of this invention is a process for reducing ferric iron to ferrous iron by treatment with microorganisms comprising forming an aqueous mixture which comprises (i) ferric iron, (ii) microoganisms operable for reducing ferric iron to ferrous iron, and (iii) a substrate which is operable as an energy source for the reduction of the ferric iron by the microorganisms, the substrate being a waste product; and maintaining the aqueous mixture under conditions operable for reducing at least a major part of the ferric iron to ferrous iron by the microbial activity of the microorganisms thereby reducing the ferrous iron.

BRIEF DESCRIPTION OF THE DRAWINGS

FIG. 1 is the conversion of Fe(III) to Fe(II) reported in the prior art.

FIGS. 4 through 10 are graphs of various parameters as a function of time in microbial reactions of Fe(III) conducted in the reactor of FIG. 3.

FIG. 4 shows concentrations of soluble lactate and ammonia during batch-reactor growth of Pseudomonas sp. 200.

FIG. 5. shows optical density, TOC, total protein (all measures of cell growth) for the growth experiment shown in FIG. 4.

FIG. 6 shows Fe(II) concentration vs. time also for the latter part of the fermentation shown in FIGS. 4 and 5.

FIG. 7 shows optical density vs. time in growth experiments using other bacterial species.

FIG. 8 shows optical density, glucose, and total ammonia in batch cultures of *Pseudomonas aeruginosa*.

FIG. 9 shows Fe(II) concentration vs. time in a batch culture of *Thiobacillus thiooxidans*.

FIG. 10 shows the development of Fe(II) in batch cultures of *Pseudomonas aeruginosa* in the presence of various concentrations of citrate ligand.

PREFERRED EMBODIMENTS

Figure 2:
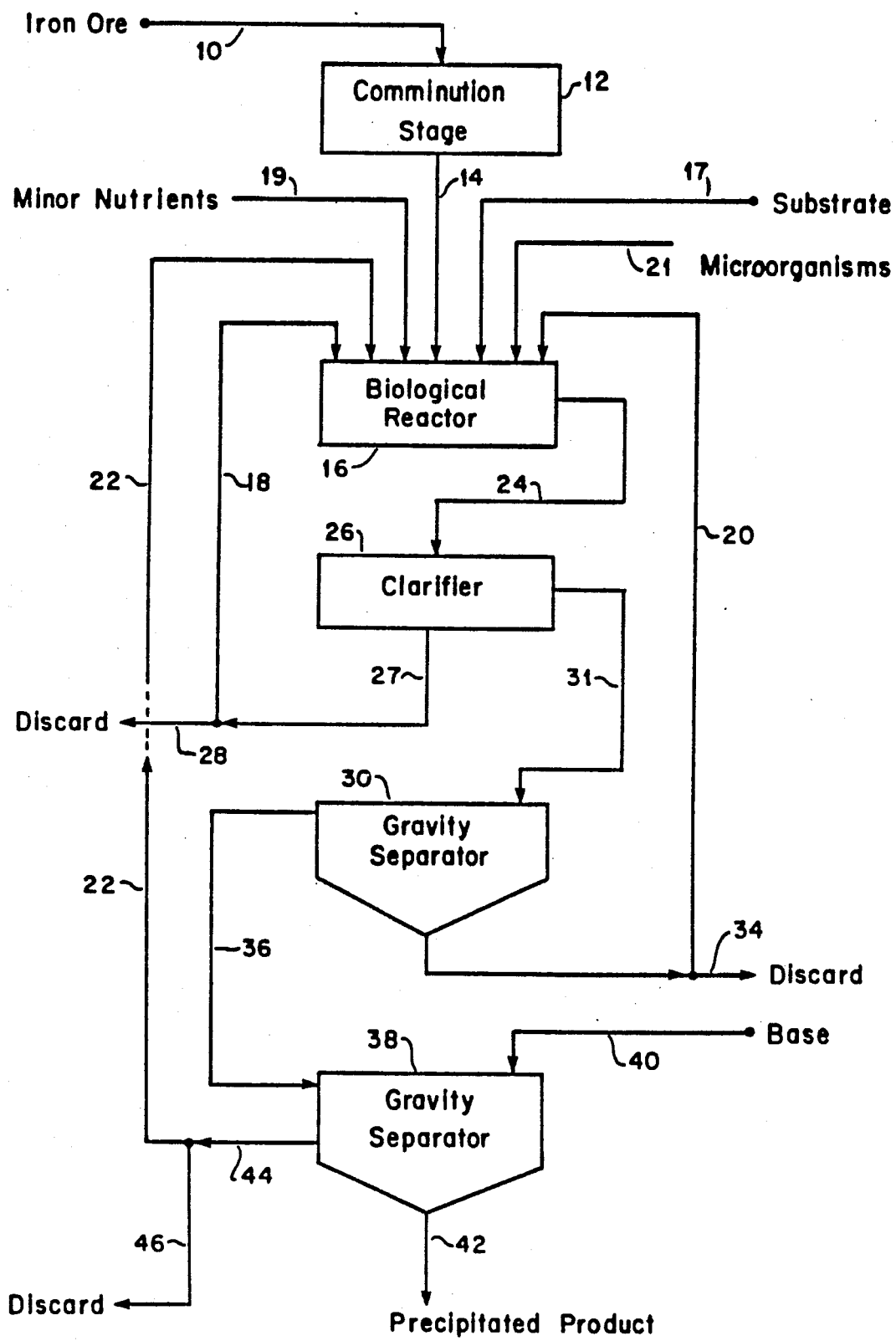
FIG. 2 is a process flow diagram for the commercial microbial reduction of iron ore.

The preferred embodiment is illustrated by the microbial reduction of iron ore. Referring to FIG. 2, iron ore in stream 10 is comminuted in comminution stage or pulverizor 12, to a predetermined particle size distribution.

Preferably the iron ore is comminuted to a particle size less than about 1 mm in diameter, and especially preferably to a particle size from about 20 to about 400 Mesh (Tyler screens, ref. W. S. Tyler Co.). Particles larger than these ranges can be used, but the subsequent microbial reduction as will be described will require a longer time. Particles smaller than these ranges can also be used but the cost of comminution operation will be increased. Preferably a particle size is chosen so that the subsequent biological reduction proceeds to substantial completion within a period of time no greater than about one day.

Iron ore particles having the desired size distribution are removed from stage 12 in stream 14 and charged to biological reactor 16 along with substrate stream 17, recycled solid-containing stream 18, recycled solids-containing stream 20, additional microorganisms with stream 21, and recycled aqueous stream 22. The contents of these streams will be described later.

Biological reactor 16 is preferably a well-mixed, continuous-flow reactor. Alternatively, in another preferred embodiment biological reactor 16 can be a slurry pipeline reactor. Naturally, this changes the overall process configuration, largely by eliminating possibilities for cell, nutrient, and substrate recycle. The aqueous slurry in reactor 16 is maintained under constant agitation to prevent settling of the solids contained therein and to ensure good contact between the iron ore particles, the microorganisms and the substrate material thereby eliminating transport limitations to the rate of ferric iron reduction.

Substrate stream 17 is preferably domestic wastewater either in its raw state or with some concentration. The major part of the microorganisms are supplied to reactor 16 in recycled stream 20 as will be further explained. These are supplemented, as required, with aerobically grown cells in stream 21. Preferably the microorganisms are Pseudomonas sp. 200 and most preferably a strain thereof which has been mutated or selected so that the strain has accelerated iron-reducing properties. If desired, minor nutrients such as phosphorous, calcium, ammonia, nitrate, molybdenum, sulfate, vitamins, and other useful minor nutrients not in sufficient supply in domestic wastewater or other media or substrate employed, and mixtures thereof can be charged to reactor 16 in stream 19.

Initially biological reactor 16 is charged with an effective amount of microorganisms operable for reducing ferric values in the iron ore to ferrous values, or alternatively the population of such microorganisms is grown to sufficient numbers during a growth period. In any event, reactor 16 is maintained under conditions which are operable to effect the microbial reduction of the iron ore particles.

In one embodiment which is especially preferred, the amount of domestic wastewater is sufficient to provide at least a major part of the energy required by the reaction mass in biological reactor 16 to reduce at least a major part of the ferric iron in the iron ore particles to ferrous iron which is soluble in the aqueous phase of the reaction mass.

A portion of the well-mixed contents of reactor 16 are continuously removed therefrom in stream 24 and charged to clarifier 26 wherein large particles are separated via gravity and small inorganic particulate matter, biomass, and the entire liquid phase are separated and charged to separator 30 via stream 31. The majority of these remaining solids are subsequently removed via sedimentation in reactor 30. Clarifier 26 preferably has a relatively high volumetric flow rate or horizontal velocity as compared to the gravity separators used later in the process. Large, predominantly inorganic solids settled in reactor 26 may be recycled via streams 27 and 18 or wasted in stream 28. Similarly, biological solids settled in reactor 30 may be recycled to the biological reactor in stream 20 or wasted in stream 34. Recycled biomass in stream 20 supplies the majority of the microorganisms required to effect the substantially complete reduction of the iron ore charged to the process in stream.

In one embodiment an initial charge of iron ore is introduced into reactor 16, by means of stream 14, ore charging is then terminated, all of the solid slurry in stream 27 is recycled to reactor 16 via stream 18 until the ferric iron content of stream 27 is substantially depleted. At this point, slurry stream 27 can then be substantially completely discarded as indicated by stream 28, and thereafter a new charge of iron ore introduced into reactor 16. Alternately, the process can be carried out with some recycling and discarding occurring simultaneously on a semi-continous basis.

Gravity separation in separator 30 is preferably conducted so as to produce an aqueous effluent, removed in stream 36, which is substantially free of undissolved solids. Stream 36 is then charged to second gravity separator 38 together with a base such as sodium hydroxide in stream 40. The base reacts with the solubilized ferrous values which were charged to separator 38 in stream 36 to produce a ferrous hydroxide precipitate which is permitted to settle to the bottom of separator 38. Preferably sufficient base is added in stream 40 to substantially precipitate all solubilized ferrous values contained in the aqueous phase in separator 38. The ferrous iron precipitate is then removed from seprator 38, preferably as a relatively concentrated slurry in stream 42. If desired, a polymer coagulant can be added to separator 38 to improve separation. A clarified water, is removed in stream 44 and, if desired, a part recycled in stream 22 and the remainder discarded after removal of harmful substances by any conventional processes (not shown in FIG. 2), as indicated by stream 46. Gravity separators 30 and 38 can be sludge thickeners.

An important advantage of this process over conventional iron ore reduction processes is that a very concentrated, iron-containing slurry can be produced without expensive operations such as centrifugation.

Another advantage associated with microbial reduction and extraction of iron ore is the fact that the product of the process, i.e. the iron-containing precipitate, is formed with relatively few impurities. Use of this material in the production of elemental iron, it is believed, would substantially decrease the total amount of chemical reductants required.

EXPERIMENTAL STUDIES

Figure 3:
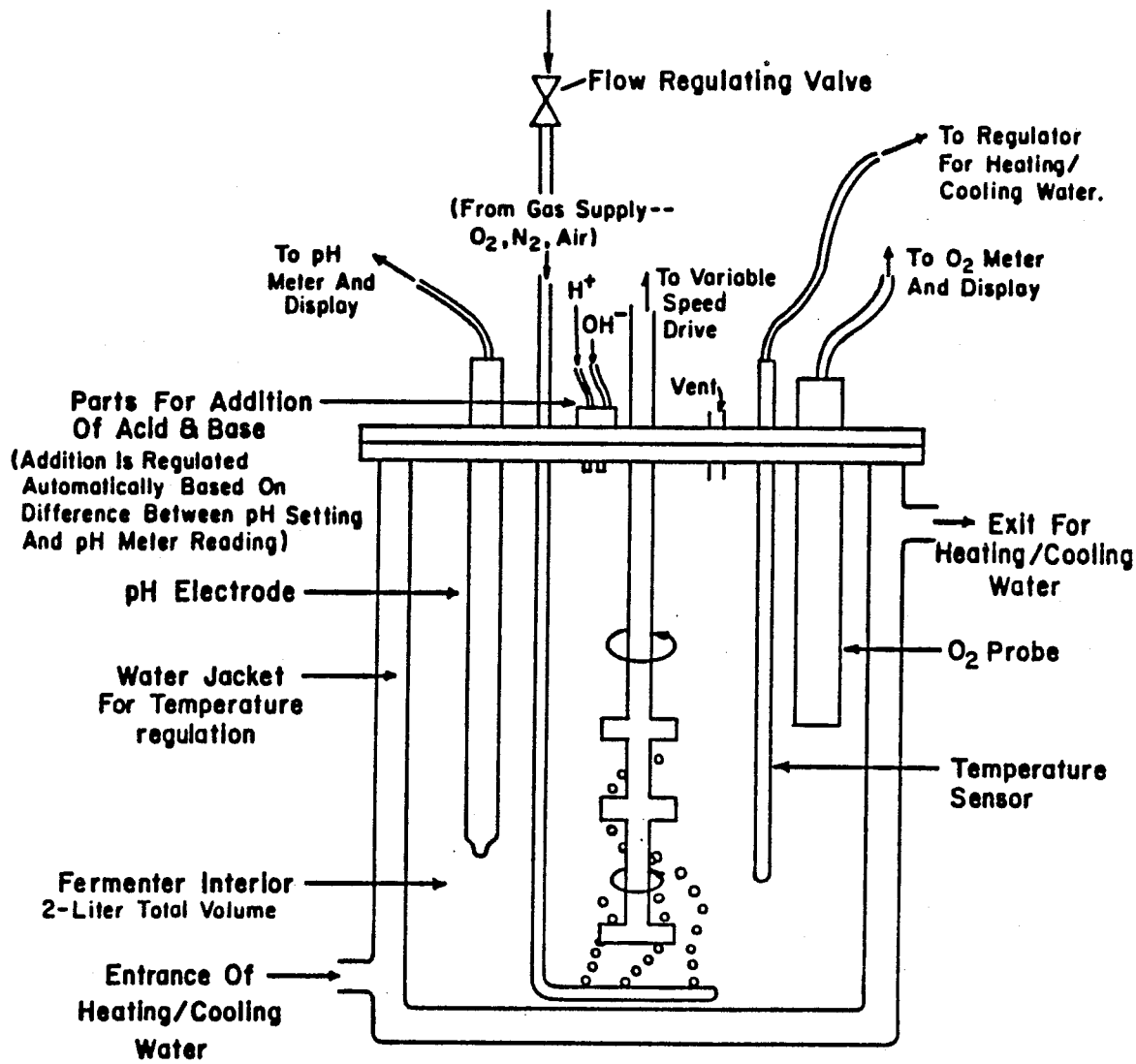
FIG. 3 is an experimental batch biological reactor.

Microbial reduction of ferric iron to ferrous iron was conducted in a 2-liter laboratory batch fermentor, Model Biostat M manufactured by B. Braun Instruments. The fermentor, illustrated in FIG. 3 is capable of providing for both temperature and pH control in the reacting volume. Aeration rate and agitation rate or mixing energy applied to the reacting mass can be varied as desired. Temperature, dissolved oxygen content, and pH of the reacting mass can be continuously measured.

One and one-half liters of growth medium A was charged to the laboratory fermentor shown in FIG. 3. The composition of growth medium A is given in Table 2. The growth medium charged to the fermentor was first adjusted to a pH of 7.2 and a temperature of 30° C., and then inoculated with Pseudomonas sp. 200 which was provided by Dr. D. W. S. Westlake of the University of Edmonton, Alberta, Canada.

During the early growth phase, also referred to as the "log growth phase" or "Phase I", the reaction mass was maintained at 30° C. and pH of 7.2 by the addition of small amounts of 2N NaOH. The reaction mass was also maintained under aerobic conditions by introducing about 0.8 liters per minute (liters/min) of oxygen gas into the fermentor through the sparger shown in FIG. 3. The oxygen gas upon discharge from the sparger formed small bubbles which were stirred into the reaction mass by the agitator shown in FIG. 3.

During Phase I, culture growth was monitored by withdrawing small samples for determination of optical density, total organic carbon ("TOC"), total solid-phase protein ("TSPP"), lactate, and ammonia content. Culture density was determined spectrophotometrically by absorbance of 600 nm radiation in a one centimeter path-length sample.

Figure 4:
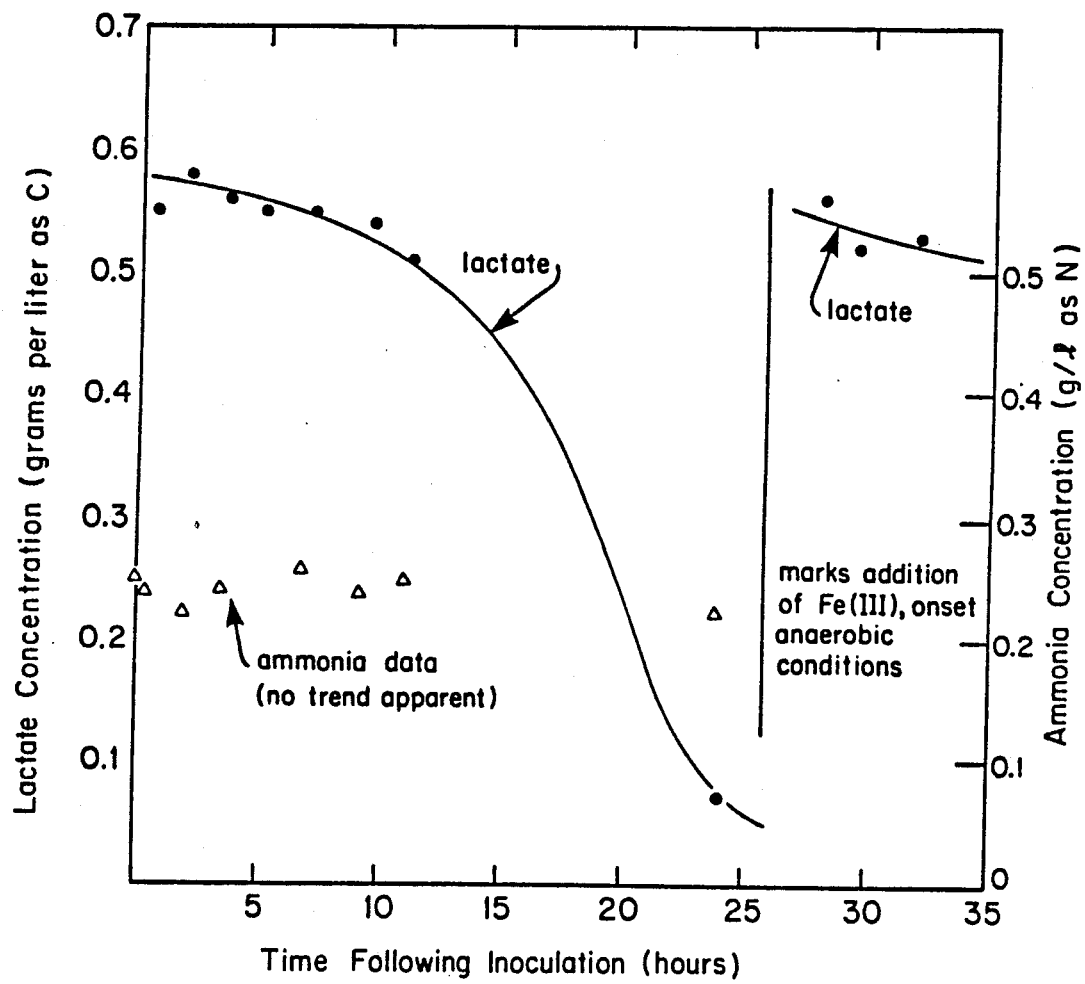

Concurrently with the above-described absorbance measurements, TOC and protein content were also determined by withdrawing and centrifuging a 4-ml sample for 25 min at 3500 rpm (3160 times gravity) in a model RC-3B Sorvall centrifuge. Such centrifuging produced a dense phase which contained the undissolved solids content of the sample and a centrate phase which contained soluble lactate and ammonia (normally present as $NH_4$). Soluble lactate and ammonia in the centrate were determined, and lactate concentration as a function of time after inoculation is shown in FIG. 4. This result will be discussed in greater detail later.

The residual solids contained in the dense phase produced by centrifugation were washed and resuspended to their original volume in saline solution (0.15M NaCl, 1 mM $MgCl_2$). The saline solution containing the residual solids, also referred to as the "solid fraction", was then analyzed for TOC content using a model DC-50 Dohrmann TOC analyzer.

The solid fraction was also used to determine TSPP content using analytical reagents and protocol obtained from Sigma Chemical Company.

Figure 5:
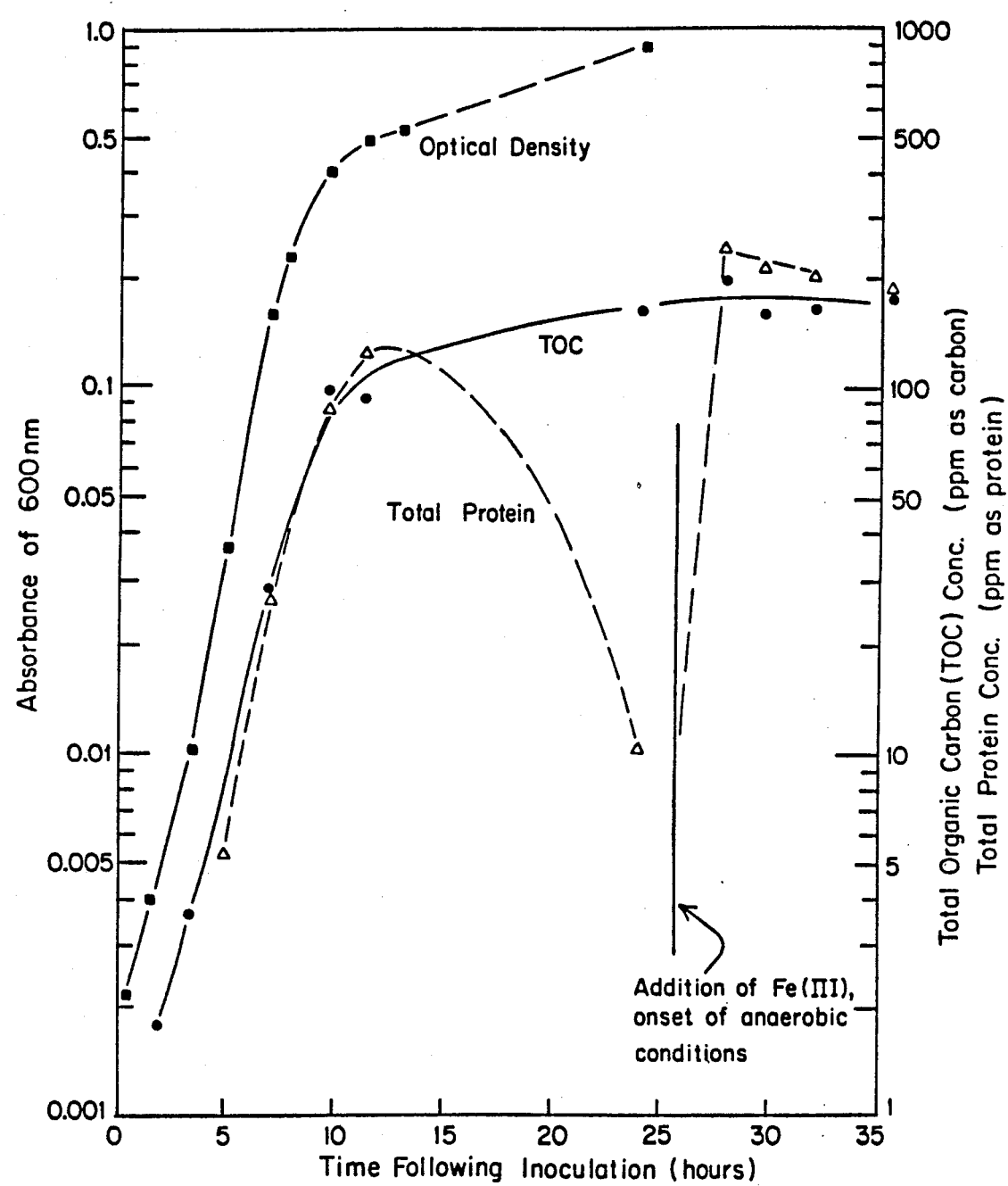

Curves representing culture or optical density, TOC, and TSPP as a function of time after inoculation with Pseudomonas sp. 200 are provided in FIG. 5. During Phase I, the doubling time or generation time for this system is about 0.8 hrs based on the optical density curve of FIG. 5 and about 1.0 hr based on the TOC curve. Data used to produce the TSPP curve are not considered to be sufficiently accurate to permit estimation of the doubling time. However, there is good agreement in doubling time calculations based on the three parameters shown in FIG. 5.

All three of the growth parameters monitored offer insight into the growth and general metabolism of the microorganism under study. As can be seen in FIG. 5, following the rapid culture growth rate of Phase I, there is a transition to stationary growth (Phase II) between about 9 and about 13 hrs after inoculation.

Again referring to FIG. 5, the supply of molecular oxygen to the fermentor was terminated after about 26 hours (well into stationary growth) and ferric iron was added as $Fe(NH_4)(SO_4)_2.12H_2O$ to the reaction mass to produce an Fe(III) concentration of about 145 mg/liter. Supplementry sodium lactate was also added at this time to replace the depleted lactate originally supplied by the growth medium. The reaction mass was henceforth maintained under anaerobic conditions by continuously purging the reacting mass with nitrogen gas at a flow rate of about 0.8 liters/min.

After addition of the ferric iron, the presence of precipitated iron hydroxide in the reaction mass impaired the usefulness of optical density measurements. However, TOC and TSPP determinations were continued since these measurements were considered reliable and convenient parameters for monitoring culture biomass and activity. Soluble lactate and ammonia were also measured throughout the anaerobic period.

Figure 6:
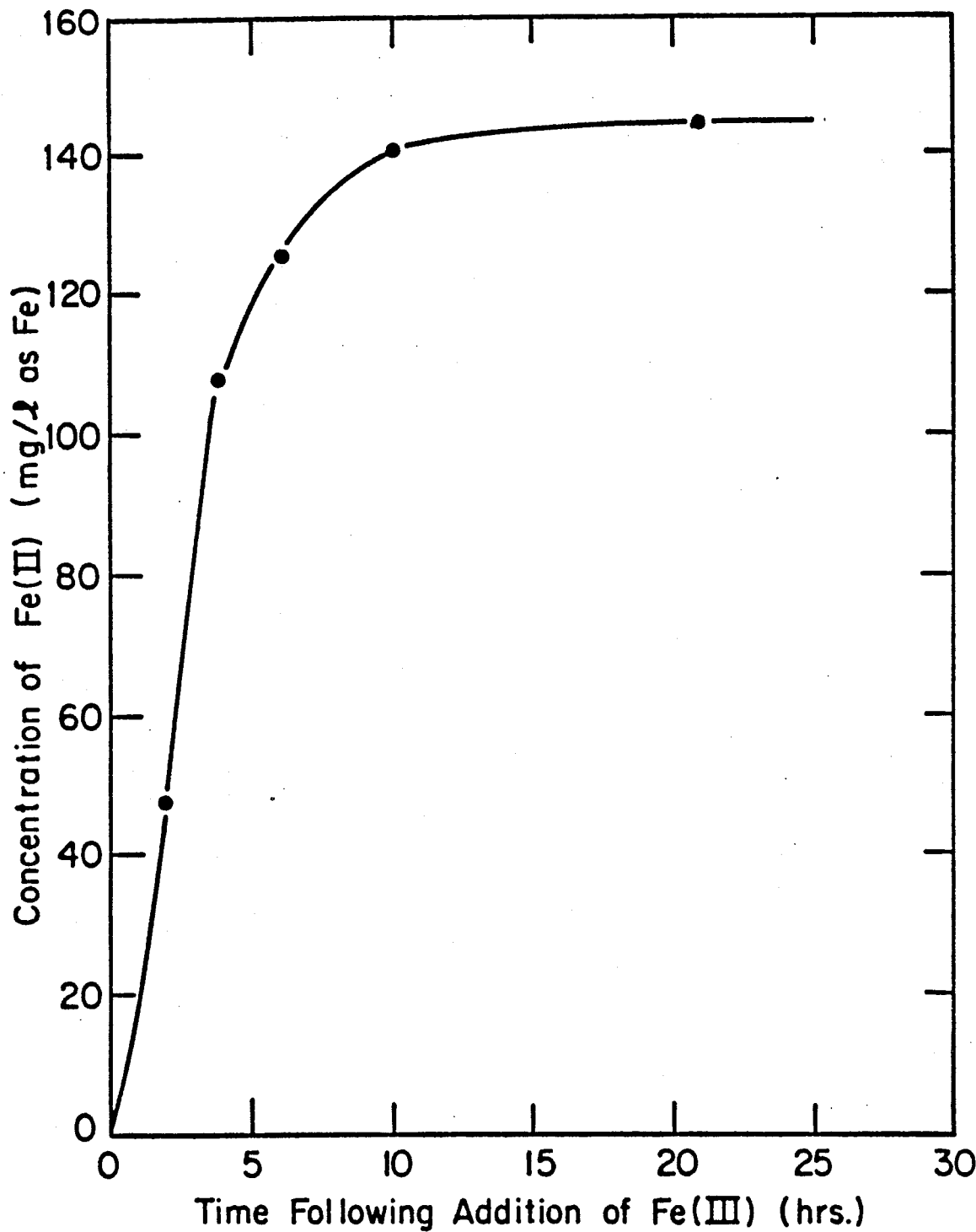

The production of soluble ferrous iron, Fe(II), in the reaction mass was monitored by periodically withdrawing small samples from the fermentor and analyzing for ferrous iron colorimetrically. Color attributable to the Fe(II)-phenanthroline complexes in the presence of excess phenanthroline was measured spectrophotometrically at a wavelength of 510 nm. The increase in ferrous iron concentration in the reacting mass is shown in FIG. 6. Stoichiometric conversion of ferric to ferrous iron was observed in the Pseudomonas sp. 200 fermentation as indicated in FIG. 6.

Returning to FIGS. 4 and 5, it is apparent that the observed drop in TSPP is related to the near exhaustion of lactate substrate. Protein levels, however, were quickly restored, even under anaerobic conditions following the addition of supplemental sodium lactate to the reacting mass. From lactate measurements, following the establishment of anaerobic conditions in this system, respiration involving Fe(III) as an electron receptor cannot provide energy for culture growth at rates comparable to those observed under aerobic conditions.

Ammonia concentrations were maintained in large excess to the needs of the microorganisms throughout the experiment. Consequently, ammonia levels remained about constant throughout the fermentation.

Furthermore, it should be noted that although no specific measures were taken to induce production of iron-reduction enzymes, only a brief lag period, on the order of one or two hours, is apparent in the curve representing iron reduction versus time (FIG. 6). In this particular system, the maximum observed rate of ferric iron reduction is about 35 mg/liter-hr, see FIG. 6.

Figure 7:
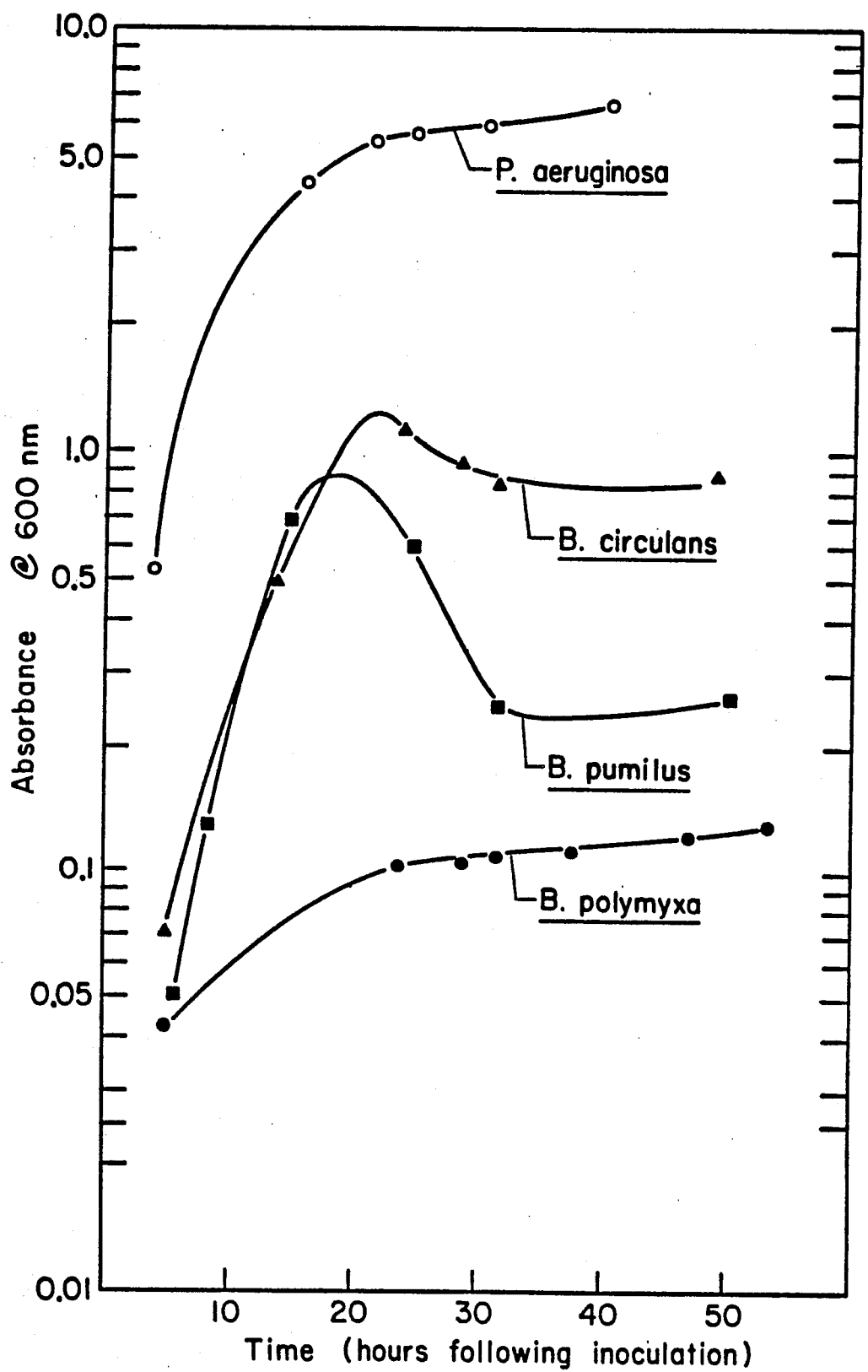
Figure 8:
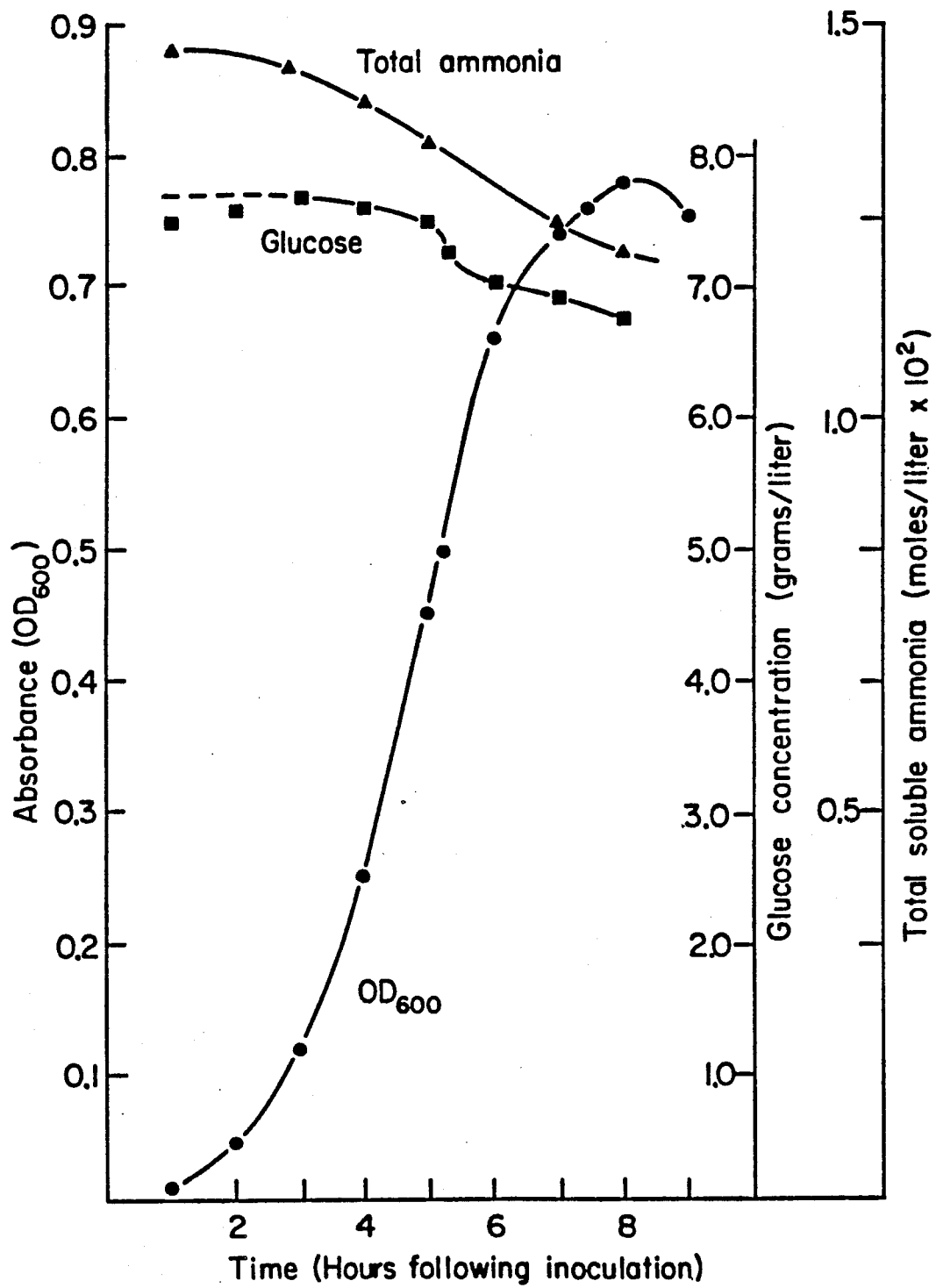

Batch reactor growth kinetics of other culture species studied under aerobic conditions are summarized in FIG. 7. The characteristics of aerobic growth and anaerobic iron reduction by *Pseudomonas aeruginosa* were studied in greater detail. Results of a single batch growth experiment are summarized in FIG. 8. The curves of FIGS. 7 and 8 permitted estimation of logarithmic growth parameters for these species; see Table 3.

Figure 9:
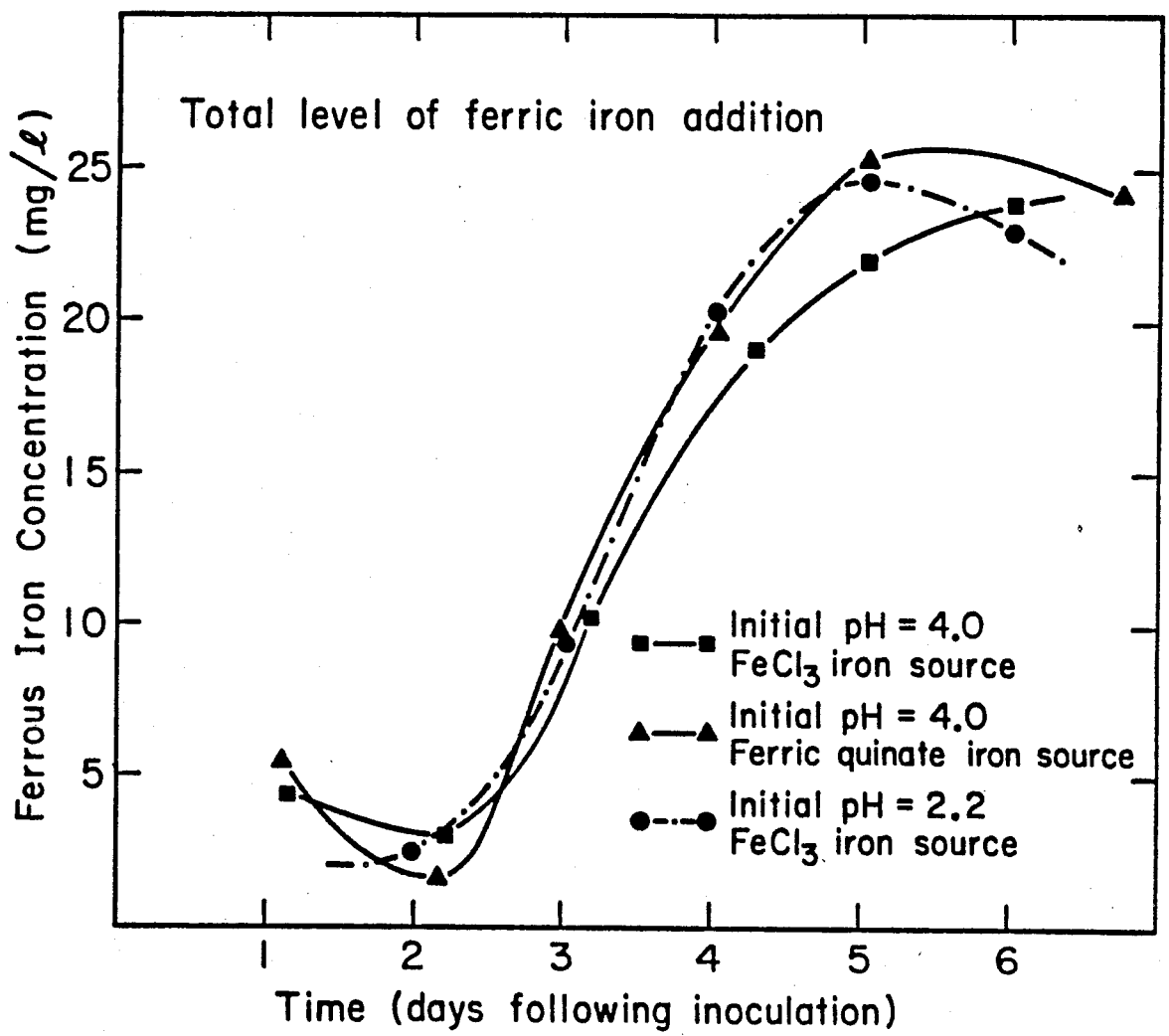

Measurement of bacterial growth on solid substrates, e.g. *Thiobacillus thiooxidans* on precipitated elemental sulfur, provided a greater challenge. In this case, the nature of the sulfur substrate precluded the use of optical density as a measure of biomass. Although measurement of solid phase total organic carbon versus time can provide the necessary growth information, such measurements were not made because of the unique problems imposed by the presence of sulfur in samples to be analyzed for carbon. This problem can be overcome by substituting a more appropriate catalyst in the total organic carbon analyzer. Batch iron reduction conducted in cultures of *Thiobacillus thiooxidans* seemed to be independent of initial pH or the presence of quinate ion, an iron ligand, in solution, as can be seen in FIG. 9.

Experiments have also been conducted to assess the role of iron-complexing ligands as promoters of iron reduction in cultures of *P. aeruginosa*. The results, summarized graphically in FIG. 10, show that complexation of Fe(III) by citrate apparently increases the availability of iron as a substrate for bacterial respiration.

ANALYSIS OF RESULTS

The short lag period and rapid rate of iron reduction evidenced in cultures of Pseudomonas sp. 200 have already been mentioned; see FIG. 6. The observed maximum rate of Fe(II) production is an order of magnitude or more faster than rate observed to date among other capable species. Such comparisons rest upon assumptions relative to the average composition (carbon and water content) of the microorganisms during stationary growth phase as will be further explained.

While we do not wish to be bound by theory, it is believed that the iron-reduction data described in FIG. 6 suggest that the rate of disappearance of Fe(III) is related to the concentration of ferric iron as, $$\frac{d[Fe(III)]}{dt} = \left(\frac{d[Fe(III)]}{dt}\right)_{max} \cdot \frac{[Fe(III)]}{K_s + [Fe(III)]} \quad \text{(Eqn. 1)}$$

Substituting $v = d[Fe(III)]/dt$ and $v_{max} = (d[Fe(III)]/dt)_{max}$, then $$\frac{1}{v} = \frac{1}{v_{max}} + \frac{K_s + [Fe(III)]}{[Fe(III)]} \quad \text{or}$$

$$\frac{1}{v} = \frac{K_s}{v_{max}} \cdot \frac{1}{[Fe(III)]} + \frac{1}{v_{max}} \quad \text{(Eqn. 2)}$$

Figure 11:
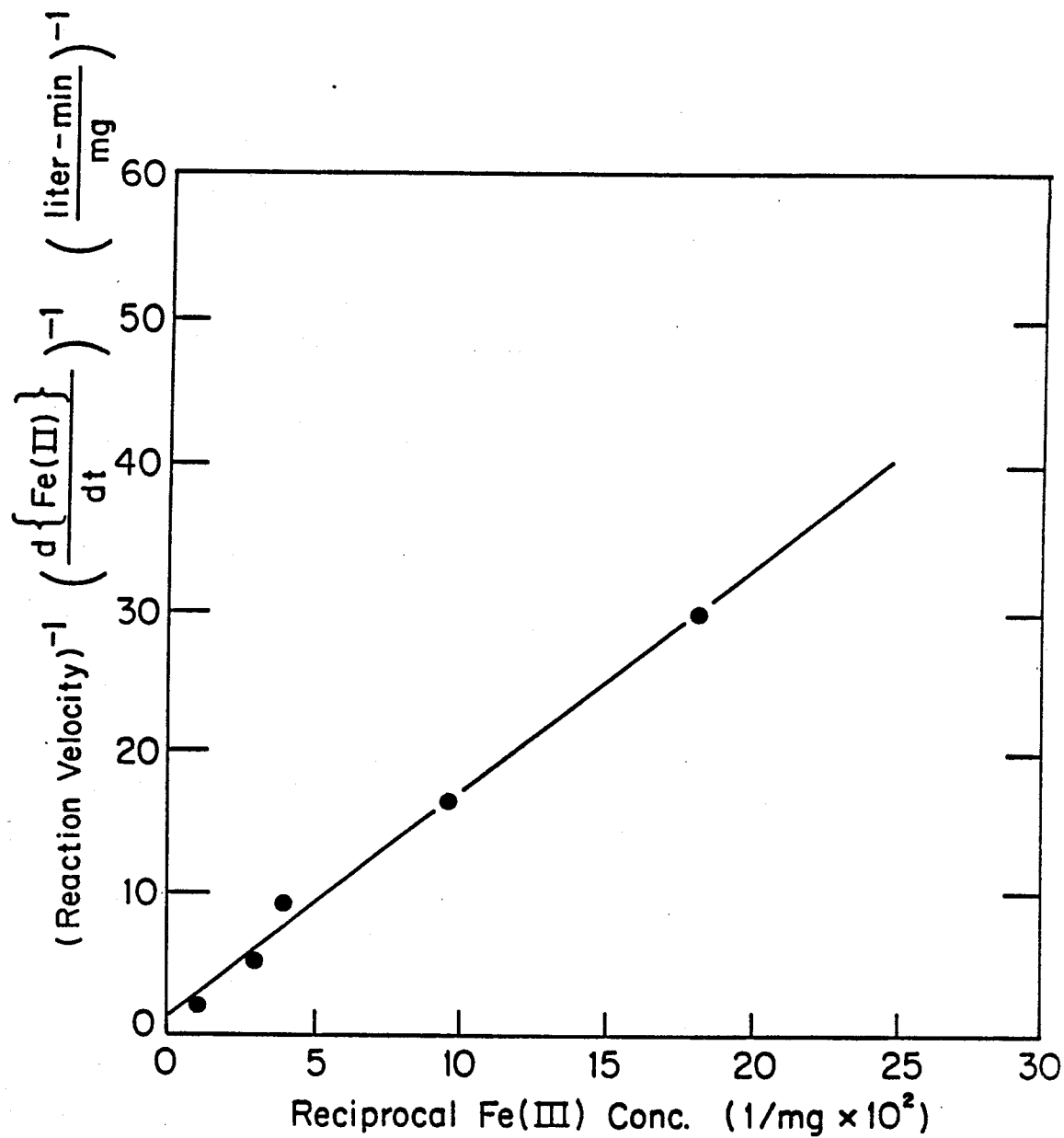
FIG. 11 shows a Lineweaver-Burk plot developed from the observed reduction of Fe(III) by Pseudomonas sp. 200.

A plot of reciprocals $1/v$ versus $1/[Fe(III)]$ (Lineweaver-Burk plot), yields estimates for both $v_{max}$ and the Michaelis constant, or half-velocity substrate concentration, $K_s$. Such a plot is shown in FIG. 11. Care should be used when interpreting these results. The linear arrangement of points provides reasonable support for the hypothesized kinetic relationship, i.e. a Michaelis-Menten dependence on substrate concentration. However, the slope and intercepts and corresponding estimates of Michaelis parameters are sensitive to the assumed initial concentration of Fe(III). As indicated on FIG. 11, the Lineweaver-Burk plot supports an estimated $v_{max}$ (maximum rate of appearance of ferrous iron) of 40 mg/liter-hr and a Michaelis constant equal to 100 mg/liter as Fe(III). While the linearity of the Lineweaver-Burk plot offers hope for this type analysis, the calculated $v_{max}$ is too low to account for iron-reduction rates observed during the first few hours following imposition of anaerobic conditions.

It is also useful to consider the energetics of bacterial respiration and the thermodynamics of dissimilative iron reduction. Half reactions relevant to the process of respiratory electron transfer include:

$\frac{1}{2}NADH = \frac{1}{2}NAD^+ + \frac{1}{2}H^+ + e$   $p\epsilon^o(w)$   (Eqn. 3)
= 5.4
$\frac{1}{4}O_2(g) + H^+ + e = \frac{1}{2}H_2O$   $p\epsilon^o(w)$   (Eqn. 4)
= 13.75
$Fe(OH)_3(amorph,s) + 3H^+ +$   $p\epsilon^o(w)$   (Eqn. 5)
= −5
$e = Fe^{2+} + 3H_2O$ Combining Equations (3) and (4) yields:

$$\tfrac{1}{2}NADH + \tfrac{1}{4}O_2(g) + \tfrac{1}{2}H^+ = \tfrac{1}{2}NAD^+ + \tfrac{1}{2}H_2O \quad \text{(Eqn. 6)}$$
$$\Delta p\epsilon^o(w) = 19.15$$

and $\Delta G^o(w)/n = -2.3\,RT\,\Delta p^o(w) = -26$ kcal per mole of electrons transferred. It is to be understood that the symbol (w) is applied to potentials and free energy values under "standard" conditions of pH=7.0, other concentrations 1 molal.

These species represent the substrates commonly encountered in both bacterial and mitochondrial respiration. Electron transfer is energetically coupled to adenosine triphosphate (ATP) generation via subsequent, cross-membrane proton transport. While measurements of bacterial P/O ratios (ratio of ATPs produced per oxygen atom utilized) have yielded variable results, energy limitations and experience dictates that under standard conditions and near-physiological pH only about 1.5 moles of ATP can be formed per mole of electrons transferred (6 moles of ATP per mole of $O_2(g)$ reduced). The free energy requirement for ADP phosphorylation under standard conditions, pH=7.0, is 7.3 kcal/mole.

Combining half-reactions leading to the reduction of Fe(III) yields:

$$\tfrac{1}{2}NADH + Fe(OH)_3 \text{ (amorph,s)} + \quad \text{(Eqn. 7)}$$
$$5/2\,H^+ = \tfrac{1}{2}NAD^+ + Fe^{2+} + 3H_2O;$$
$$\Delta p\epsilon^o(w) = 0.4 \text{ and}$$
$$\Delta G^o(w)/n = -0.54 \text{ kcal/mole of electrons transferred}$$
(or mole of ferric iron reduced.)

Thus dissimilative iron reduction is capable of generating far less useable chemical energy than does aerobic respiration. For conditions other than standard conditions, Equation 7 becomes:

$$\Delta G/n = -0.54 + \quad \text{(Eqn. 8)}$$
$$2.3\,RT\,\log\{(10^{-7}/[H^+])^{5/2}[NAD^+]^{\tfrac{1}{2}}[Fe^{2+}]/[NADH]^{\tfrac{1}{2}}\}$$

Based on this analysis, it is concluded that low Fe(II) concentration, and pH values below 7.0, make dissimilative iron reduction more energetically favorable. For instance, when $[Fe^{2+}] = 10^{-3}M$, pH=6.0, $[NAD^+] = [NADH]$, then $\Delta G = -8$ kcal/more of electrons transferred. Under such conditions, coupled ADP phosphorylation is at least energetically feasible.

It is also possible that under anaerobic conditions all chemical energy production is via substrate level phosphorylation and dissimilative iron reduction serves only as a means for dissipating the reducing power generated in other metabolic events. With a little speculation regarding catabolic processes in Pseudomonas sp. 200, it is possible to break the free energy content of lactate oxidation down into the components listed in Table 4.

From Table 4 and calculations reviewed to this point, the limitations of dissimilative iron reduction are fairly clear. If it is assumed that respiration involving Fe(III) serves only to dissipate excess reducing power, then stoichiometric considerations dictate that as little as 1 mole of phosphodiester bonds will result from breakdown of a mole of lactate. At its limit (oxidation of lactate to $CO_2$), the oxidation would result in reduction of perhaps 12 moles of Fe(III), although this might be optimistic if a variety of partially oxidized metabolic by-products are secreted into solution under anaerobic conditions.

If, however, ATP generation associated with dissimilative iron reduction is energetically important and each NADH oxidation results in phosphorylation of an ADP molecule, then the useable energy generated from the oxidation of lactate could increase five-fold.

Assuming that net growth and associated anabolic energy requirements are negligible in the absence of molecular oxygen, then the maximum observed rate of useable energy generation for cell maintenance would be on the order of:

$$\frac{0.06\,g}{\text{liters-hr}} \cdot \frac{1 \text{ mole Fe}}{55.85\,g} \cdot \frac{5 \text{ moles ATP generated}}{12 \text{ moles of Fe(III) reduced}} \cdot \quad \text{(Eqn. 9)}$$

$$\frac{7.3 \text{ kcal}}{\text{mole of ATP}} =$$

3.25 cal/liter-hr or 0.45 mmol ATP/liter-hr.

If we adopt a maintenance energy coefficient of about 1 m mole ATP/g-hr (at the lower limit of figures cited by Atkinson and Mavituna, 1983, as typical for microbial fermentations) it becomes apparent that a rather generous set of assumptions is required if dissimilative iron reduction is to account for maintenance energy requirements alone in the Pseudomonas sp. 200 fermentation described herein. As a related matter, the dry-weight concentration of cells at the close of the fermentation was on the order of 0.3 grams per liter, see FIG. 5, assuming organic carbon comprises 50 percent of cell dry weight.

In summary, we have observed that under most circumstances, optical density, total particulate organic carbon, and total protein exhibit reasonable agreement as indicators of culture biomass. Through exponential growth phase, optical density offers advantages of convenience and accuracy; following Fe(III) addition and establishment of anaerobic conditions, TOC or protein measurements must be utilized due to the presence of precipitated iron hydroxide in suspension. Protein measurements appear to offer unique insights into culture activity.

Pseudomonas sp. 200 stands alone among bacteria thus far investigated for their iron-reducing abilities. Observed iron reduction is an order of magnitude faster than rates for other microorganisms studied.

TABLE 1

| | Bacteria Screened for Iron Reduction Capability | | | |
|---|---|---|---|---|
| Species | Classification by Carbon & Energy Source | Oxygen Requirement | Classification | Comment |
| Bacillus pumilus | Chemoheterotroph | Not fermentive; no nitrate reductase activity | Gram positive | Soil bacteria; spore formers |
| Bacillus polymyxa | Chemoheterotroph | Will ferment glucose; nitrate reductase activity | Gram positive | Soil bacteria; spore formers |

TABLE 1-continued
Bacteria Screened for Iron Reduction Capability

| Species | Classification by Carbon & Energy Source | Oxygen Requirement | Classification | Comment |
|---|---|---|---|---|
| Bacillus circulans | Chemoheterotroph | Strain dependent fermentation and nitrate reductase activity | Gram positive | Soil bacteria; spore formers |
| Pseudomonas aeruginosa | Chemoheterotroph | Not fermentive; nitrate reductase activity | Gram negative | Found in lakes, soils, sewage |
| Pseudomonas sp. 200 | Chemoheterotroph | Grows aerobically; capable of dissimilative iron reduction | Gram negative | Isolated from crude oil |
| Thiobacillus thiooxidans | Autotroph Lithotroph | Obligate aerobe | Gram negative | Energy from sulfur oxidation; acidophile |
| Sulfolobus acidocaldarius | Facultative autotroph | Microaerophilic (probably) | — | thermophilic, acidophilic |
| Bacillus acidocaldarius | Chemoheterotroph | Microaerophilic (probably) | Gram variable | Thermophilic |

TABLE 2
Growth Medium A-Used to grow Pseudomonas sp. 200 in batch fermentations

| Grams per liter | Component |
|---|---|
| 0.6 | $K_2HPO_4$ |
| 2.0 | $Na_2SO_4$ |
| 1.0 | $NH_4Cl$ |
| 0.15 | $CaCl$ |
| 0.1 | $MgSO_4 \cdot 7H_2O$ |
| 0.193 | $FeCl_3 \cdot 6H_2O$ |
| 0.6 | Yeast extract |
| (1) | Sodium Lactate |

(1) 3 milliliters per liter of a syrup which is 60% by weight of sodium lactate

TABLE 3
Growth Parameters for Selected Iron-Reducing Bacteria

| Species | Doubling Time (hours) | Experimental Growth Rate Constant |
|---|---|---|
| Bacillus circulans | 2 | 0.35 |
| Bacillus pumilus | 2 | 0.35 |
| Bacillus polymyxa | 2 | 0.35 |
| Pseudomonas aeruginosa | 1.1 | 0.63 |
| Bacillus acidocaldarius | 0.7 | 1.0 |

TABLE 4
Component Free Energy Changes during the Oxidation of Lactate

| Component | Theoretical ΔG (w) | Phosphodiester Bonds Produced |
|---|---|---|
| (1) Lactate to pyruvate conversion | −58 kcal/mole[a] | unknown[d] |
| (2) Pyruvate to $CO_2$ conversion (less energy of NADH, $FADH_2$ oxidation) | −37 kcal/mole[c] | 1[e] |
| (3) Membrane-mediated electron transfer | −245 kcal/mole[b] | 14[f] |

TABLE 4-continued
Component Free Energy Changes during the Oxidation of Lactate

| Component | Theoretical ΔG (w) | Phosphodiester Bonds Produced |
|---|---|---|
| reactions | | |

[a] Based on relative free energies for complete oxidation of lactic and pyruvic acids. Atkinson and Mavituna (1983).
[b] Calculation is based upon generation of 4 moles of NADH and one mole of $FADH_2$ in the TCA conversion of one mole of pyruvate to $CO_2$. $\Delta G^o(w)$ for the oxidation of NADH by $O_2(g)$ is −52.6 kcal/mole oxidized (Stryer, 1981). $\Delta G^o(w)$ for the oxidation of $FADH_2$ was crudely estimated at −52.6 (⅔) ≈ −35 kcal/mole oxidized.
[c] Obtained via difference - total energy of pyruvate oxidation less energies of NADH, $FADH_2$ oxidations. Note - energy of pyruvate oxidation by $O_2$ is $\Delta G^o(w)$ = −282 kcal/mole (Atkinson and Mavituna, 1983).
[d] Metabolic pathway for Pseudomonas conversion of lactate to pyruvate was not found in portion of literature search conducted to date. In the metabolism of many organisms, however, the conversion is accompanied by generation of $CO_2(g)$ and reduction of $NAD^+$ to NADH. Such a conversion would result in formation of no phosphodiester bonds.
[e] Results from the substrate-level phosphorylation of GDP to GTP within the TCA cycle.
[f] Figures representative of mitochondrial respiration (Stryer, 1981).

What is claimed is:

1. A process for forming and separating an iron-containing precipitate from iron ore by treatment with microorganisms comprising:

(a) forming iron ore particles which contain ferric iron;

(b) forming an aqueous mixture which comprises (i) said iron ore particles thusly formed in step (a), (ii) an effective amount of microorganisms operable for reducing said ferric iron of said iron ore particles to ferrous iron, (iii) an effective amount of a substrate operable for producing at least a major part of the energy required by said mixture to reduce at least a major part of said ferric iron of said iron ore particles to ferrous iron, said substrate being a waste product;

(c) maintaining said aqueous mixture for a predetermined period of time under conditions of temperature and pressure and under an atmospheric environment, operable for reducing at least a major part of said ferric iron of said iron ore particles to ferrous iron which is soluble in the aqueous phase of said aqueous mixture by the microbial activity of said microorganisms;

(d) separating an aqueous phase containing said soluble ferrous iron from said aqueous mixture; and (e) forming and separating an iron-containing precipitate from said separated aqueous phase.

2. The process of claim 1, wherein said forming of said precipitate in step (e) is by adding a base to said separated aqueous phase to precipitate a ferrous iron precipitate.

3. The process of claim 1, further comprising adding a supplementary amount of a minor nutrient to said aqueous mixture formed in step (b).

4. The process of claim 3, wherein said minor nutrient is selected from the group consisting of phosphorous, calcium, ammonium compounds, nitrate, molybdenum, sulfate compounds, vitamins, and mixtures thereof.

5. The process of claim 1, further comprising producing said microorganisms in an aerobic environment by inoculating an aqueous growth medium with an inoculating amount of said microorganisms thereby forming a growth mixture; maintaining said growth mixture under aerobic conditions operable to substantially increase the population of said microorganisms; and introducing said thusly produced microorganisms in a feedstream into said aqueous mixture as said effective amount of said microorganisms mentioned in step (b).

6. The process of claim 1, wherein said predetermined period of time referred to in step (c) is no greater than about one day, and wherein said conditions are a temperature from about 40 F. to about 160 F., and an absolute pressure of from about one atmosphere.

7. The process of claim 1, wherein said maintaining of said aqueous mixture in step (c) is conducted in a system which comprises a well mixed continuous-flow reactor or a slurry pipeline.

8. A process for recovering a slurry which comprises a ferrous iron-containing precipitate from iron ore comprising:
(a) comminuting iron ore which contains ferric iron into particles;
(b) forming an aqueous mixture which comprises (i) said particles, (ii) an effective amount of microorganisms operable for reducing said ferric iron of said particles to ferrous iron, (iii) an effective amount of a substrate operable for producing at least a major part of the energy required by said mixture to reduce at least a major part of said ferric iron of said particles to ferrous iron, said substrate being a waste product;
(c) maintaining said aqueous mixture for a predetermined period of time under conditions of temperature and pressure, and in an anaerobic environment, operable for reducing at least a major part of said ferric iron of said particles to ferrous iron which is soluble in the aqueous phase of said aqueous mixture by the microbial activity of said microorganisms;
(d) separating said aqueous mixture containing said soluble ferrous iron into (i) an aqueous phase which comprises said soluble ferrous iron and which is substantially free of undissolved solids, and (ii) a slurry fraction which contains undissolved solids;
(e) treating said separated aqueous phase which comprises said soluble ferrous iron with a reagent operable for forming a precipitate which contains a major part of the iron component of said ferrous iron thereby forming a mixture comprising an iron-containing precipitate and an aqueous phase having a reduced amount of dissolved iron; and
(f) recovering a slurry which comprises said iron-containing precipitate from said mixture formed in step (e).

9. The process of claim 8, wherein said maintaining of said aqueous mixture in step (c) is conducted in a system which comprises a well mixed continuous-flow reactor or a slurry pipeline.

10. The process of claim 8, wherein said reagent for treating said separated aqueous phase in step (e) is sodium hydroxide and said iron-containing precipitate is ferrous hydroxide.

11. The process of claim 8, wherein said separating of said aqueous mixture in step (d) comprises gravity separation, and wherein said recovering of said slurry in step (f) comprises gravity separation.

12. The process of claim 8, further comprising adding said slurry fraction separated in step (d) to said aqueous mixture formed in step (b).

13. The process of claim 8, further comprising separating, after step (c), biomass from said aqueous mixture and recycling said separated biomass to step (b) as said microorganisms.

14. The process of claim 8, further comprising adding a supplementary amount of a minor nutrient to said aqueous mixture formed in step (b).

15. The process of claim 14, wherein said minor nutrient is selected from the group consisting of phosphorous, calcium, ammonium compounds, nitrate, molybdenum, sulfate compounds, vitamins, and mixtures thereof.

16. The process of claim 8, further comprising producing said microorganisms in an aerobic environment by inoculating an aqueous growth medium with an inoculating amount of said microorganisms thereby forming a growth mixture; maintaining said growth mixture under aerobic conditions operable to substantially increase the population of said microorganisms; and introducing said thusly produced microorganisms in a feedstream into said aqueous mixture as said effective amount of said microorganisms mentioned in step (b).

17. The process of claim 8, wherein said predetermined period of time referred to in step (c) is no greater than about one day, and wherein said conditions are a temperature from about 40 F. to about 160 F., and an absolute pressure of from about one atmosphere.

18. The process of claim 8, wherein said forming of said precipitate in step (e) is by adding a base to said separated aqueous phase to precipitate a ferrous iron precipitate.

19. The process of any one of claims 1 or 8, wherein said waste substrate is selected from the group consisting of carbonaceous waste products, substances containing partially reduced sulfur forms, and mixtures thereof.

20. The process of any one of claims 1 or 8, wherein said waste substrate is a carbonaceous waste product selected from the group consisting of agricultural waste, forest industry waste, dairy waste, brewery waste, chemical industry waste, wastewaters, and mixtures thereof.

21. The process of any one of claims 1 or 8, wherein a major amount of said waste substrate is a waste product selected from the group consisting of sugar beet waste, sugar cane waste, rice hulls, dairy whey, tree bark, paper waste, pulp waste, domestic wastewaters, industrial wastewaters, textile mill waste, poultry processing waste, meat processing waste, fruit and vegetable processing waste, livestock feed lot waste, cannery waste, slaughterhouse waste, and mixtures thereof.

22. The process of any one of claims 1 or 8, wherein said microorganisms are selected from the group consisting of *Bacillus circulans, Bacillus pumilus, Bacillus polymyxa, Pseudomonas aeruginosa,* Pseudomonas sp. 200, *Bacillus acidocaldarius, Aerobacter aerogenes, Esherichia coli, Bacillus cereus, Bacillus mesentericus, Clostridium polymyxa, Bacillus centrosporus, Bacillus megaterium, Clostridium butyricum, Clostridium saccharobutyricum,* Bacillus 29, Bacillus 29A and mixed cultures of the aforementioned microorganisms.

23. The process of any one of claims 1 or 8, wherein said microorganisms are strains of organisms which have been mutated or selected so that said strains have enhanced iron reducing properties, said organisms being selected from the group consisting of *Bacillus circulans, Bacillus pumilus, Bacillus polymyxa, Pseudomonas aeruginosa,* Pseudomonas sp. 200, *Bacillus acidocaldarius, Aerobacter aerogenes, Esherichia coli, Bacillus cereus, Bacillus mesentericus, Clostridium polymyxa, Bacillus centrosporus, Bacillus megaterium, Clostridium butyricum, Clostridium saccharobutyricum,* Bacillus 29, Bacillus 29A, and mixed cultures of the aforementioned organisms.

24. A process for recovering a slurry which comprises a ferrous iron-containing precipitate from iron ore comprising:
    (a) comminuting iron ore which contains ferric iron into particles;
    (b) forming an aqueous mixture which comprises (i) said particles, (ii) an effective amount of microorganisms operable for reducing said ferric iron of said particles to ferrous iron, wherein said microorganisms are selected from the group consisting of *Bacillus circulans, Bacillus pumilus, Bacillus polymyxa, Pseudomonas aeruginosa,* Pseudomonas sp. 200, *Bacillus acidocaldarius, Aerobacter aerogenes, Esherichia coli, Bacillus cereus, Bacillus mesentericus, Clostridium polymyxa, Bacillus centrosporus, Bacillus megaterium, Clostridium butyricum, Clostridium saccharobutyricum,* Bacillus 29, Bacillus 29A and mixed cultures of the aforementioned microorganisms, (iii) an effective amount of a substrate operable for producing at least a major part of the energy required by said mixture to reduce at least a major part of said ferric iron of said particles to ferrous iron, said substrate being a carbonaceous waste product selected from the group consisting of agricultural waste, forest industry waste, dairy waste, brewery waste, chemical industry waste, wastewaters, and mixtures thereof,
    (c) maintaining said aqueous mixture for a predetermined period of time under conditions of temperature and pressure, and in an anaerobic environment, operable for reducing at least a major part of said ferric iron of said particles to ferrous iron which is soluble in the aqueous phase of said aqueous mixture by the microbial activity of said microorganisms, wherein said conditions are a temperature from about 40° F. to about 160° F. and an absolute pressure of about one atmosphere;
    (d) separating said aqueous mixture containing said soluble ferrous iron into (i) an aqueous phase which comprises said soluble ferrous iron and which is substantially free of undissolved solids, and (ii) a slurry fraction which contains undissolved solids;
    (e) treating said separated aqueous phase which comprises said soluble ferrous iron with a reagent operable for forming a precipitate which contains a major part of the iron component of said ferrous iron thereby forming a mixture comprising an iron-containing precipitate and an aqueous phase having a reduced amount of dissolved iron; and
    (f) recovering a slurry which comprises said iron-containing precipitate from said mixture formed in step (e).

25. The process of clam 24, wherein said waste substrate is a waste product selected from the group consisting of sugar beet waste, sugar cane waste, rice hulls, dairy whey, tree bark, paper waste, pulp waste, domestic wastewaters, industrial wastewaters, textile mill waste, poultry processing waste, meat processing waste, fruit and vegetable processing waste, livestock feed lot waste, cannery waste, slaughterhouse waste, and mixtures thereof.

26. The process of claim 24, further comprising adding a supplementary amount of a minor nutrient to said aqueous mixture formed in step (b).

27. The process of claim 26, wherein said minor nutrient is selected from the group consisting of phosphorous, calcium, ammonium compounds, nitrate, molybdenum, sulfate compounds, vitamins, and mixtures thereof.

28. The process of claim 24, further comprising producing said microorganisms in an aerobic environment by inoculating an aqueous growth medium with an inoculating amount of said microorganisms thereby forming a growth mixture; maintaining said growth mixture under aerobic conditions operable to substantially increase the population of said microorganisms; and introducing said thusly produced microorganisms in a feedstream into said aqueous mixture as said effective amount of said microorganisms mentioned in step (b).

29. The process of claim 24, wherein said microorganisms have been mutated or selected so that said strains have enhanced iron reducing properties.

30. The process of claim 24, wherein a major amount of said substrate is a carbonaceous waste product selected from the group consisting of sugar beet waste, sugar cane waste, rice hulls, dairy whey, tree bark, paper waste, pulp waste, domestic wastewaters, industrial wastewaters, textile mill waste, poultry processing waste, meat processing waste, fruit and vegetable processing waste, livestock feed lot waste, cannery waste, slaughterhouse waste, and mixtures thereof.

31. The process of claim 24, wherein said predetermined period of time referred to in step (c) is no greater than about one day, and wherein said conditions are a temperature from about 40 F. to about 160 F., and an absolute pressure of from about one atmosphere.

32. The process of claim 24, wherein said maintaining of said aqueous mixture in step (c) is conducted in a system which comprises a well mixed continuous-flow reactor or a slurry pipeline.

33. The process of claim 24, wherein said forming of said precipitate in step (e) is by adding a base to said separated aqueous phase to precipitate a ferrous iron precipitate.

* * * * *